(12) United States Patent
Tachizaki

(10) Patent No.: US 12,397,144 B2
(45) Date of Patent: Aug. 26, 2025

(54) CONNECTING DEVICE

(71) Applicant: JMS Co., Ltd., Hiroshima (JP)

(72) Inventor: Hitoshi Tachizaki, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 712 days.

(21) Appl. No.: 17/788,206

(22) PCT Filed: Dec. 14, 2020

(86) PCT No.: PCT/JP2020/046571
§ 371 (c)(1),
(2) Date: Jun. 22, 2022

(87) PCT Pub. No.: WO2021/131860
PCT Pub. Date: Jul. 1, 2021

(65) Prior Publication Data
US 2023/0048460 A1 Feb. 16, 2023

(30) Foreign Application Priority Data
Dec. 27, 2019 (JP) .................... 2019-239594

(51) Int. Cl.
*A61M 39/10* (2006.01)
*A61M 39/24* (2006.01)
*A61M 39/26* (2006.01)

(52) U.S. Cl.
CPC ........ *A61M 39/1011* (2013.01); *A61M 39/26* (2013.01); *A61M 2039/1083* (2013.01);
(Continued)

(58) Field of Classification Search
CPC .............. A61M 39/1011; A61M 39/26; A61M 2039/1083; A61M 2039/1088;
(Continued)

(56) References Cited

U.S. PATENT DOCUMENTS

| | | | |
|---|---|---|---|
| 2010/0283238 A1* | 11/2010 | Deighan | A61M 39/10 285/328 |
| 2018/0064605 A1* | 3/2018 | Noguchi | A61J 1/2048 |
| 2018/0064923 A1* | 3/2018 | Takeuchi | F16L 37/133 |

FOREIGN PATENT DOCUMENTS

| | | |
|---|---|---|
| JP | 2013-252165 | 12/2013 |
| JP | 2017-209149 | 11/2017 |

(Continued)

OTHER PUBLICATIONS

International Search Report issued in International Application No. PCT/JP2020/046571, Feb. 9, 2021, 4 pages.

*Primary Examiner* — Jason E Flick
(74) *Attorney, Agent, or Firm* — HSML P.C.

(57) ABSTRACT

A male connector (100) includes a first fitting structure (127) on an inner circumferential surface of a hood (120) surrounding a male member (110). A female connector (200) includes a rotating cylinder (250) rotatably provided on a female connector main body (210) that includes a partition member (220) made of an elastic material. A second fitting structure (257) is provided on an outer circumferential surface of the rotating cylinder. When the male connector is connected to the female connector, the male member passes through a slit (223) of the partition member, the female connector is inserted into the hood, and the first fitting structure fits to the second fitting structure.

11 Claims, 12 Drawing Sheets

(52) U.S. Cl.
CPC ............... *A61M 2039/1088* (2013.01); *A61M 2039/2426* (2013.01)

(58) Field of Classification Search
CPC .. A61M 2039/2426; A61M 2039/1027; A61M 2039/1038; A61M 2039/1094; A61M 2039/268; A61M 39/10; A61M 2039/1016; A61M 39/1055; A61M 2039/1072; A61M 2039/1077; A61M 2039/267; A61M 39/165
See application file for complete search history.

(56) References Cited

FOREIGN PATENT DOCUMENTS

| | | |
|---|---|---|
| WO | 2016/133139 | 8/2016 |
| WO | 2016/152801 | 9/2016 |
| WO | 2016/174032 | 11/2016 |

* cited by examiner

CONNECTING DEVICE

TECHNICAL FIELD

The present invention relates to a connecting device constituted by a male connector and a female connector.

BACKGROUND ART

To administer a drug solution to a patient, first, the prepared drug solution is put into a syringe by suction, and then, the drug solution is administered to the patient through a catheter (or a tube) placed (or inserted) in the patient. The drug solution may contain a hazardous drug such as an anticancer drug. If the hazardous drug leaks to the outside, a worker will be exposed to the drug. In order to prevent drug exposure during drug transfer, it is common to transfer a drug solution using a closed-system connecting device.

Patent Document 1 discloses an example of a closed-system connecting device constituted by a male connector and a female connector.

The male connector of Patent Document 1 includes a rod-shaped male member and a shield that covers the male member. A flow channel through which a drug solution flows is formed within the male member. The flow channel is in communication with the outside via a lateral hole, the lateral hole being formed near a distal end of the male member and extending in the radial direction. The shield is made of an elastic material such as rubber, and a hole through which the male member can pass is formed at a distal end of the shield. In an initial state, an inner circumferential surface of the hole closes the lateral hole of the male member in a liquid-tight manner. When the male connector is connected to the female connector, the shield is compressively deformed in a longitudinal direction of the male connector, and the male member passes through the hole of the shield and protrudes from the shield. When the male connector is disconnected from the female connector, the shield immediately expands to the initial state. The male member is accommodated in the shield, and the lateral hole is closed by the shield.

The female connector of Patent Document 1 includes a self-closing partition member (septum) that is made of an elastic material such as rubber and in which a slit is formed. When the male connector is connected to the female connector, the male member of the male connector is inserted into the slit of the partition member. When the male connector is disconnected from the female connector, the slit immediately returns to its initial state, and the slit is closed in a liquid-tight manner.

The connecting device of Patent Document 1 can be used to transfer a drug solution. For example, it is possible to provide the male connector at a barrel end of a syringe and the female connector at an upstream end of a catheter placed in a patient. It is possible to connect the male connector to the female connector and administer a drug solution stored in the syringe to the patient through the catheter. When the male connector is disconnected from the female connector, the male member is accommodated in the shield, and the slit of the female connector is closed. Therefore, the drug solution is prevented from leaking to the outside from each of the male connector and the female connector.

CITATION LIST

Patent Documents

Patent Document 1: WO 2016/133139A1
Patent Document 2: WO 2016/152801A1

DISCLOSURE OF INVENTION

Problem to be Solved by the Invention

For example, an anticancer drug may be administered to a vein, bladder, medullary cavity, gastrointestinal tract, or the like, depending on the type and location of the cancer. A catheter is placed in a patient such that its distal end reaches the administration site of the anticancer drug. From the viewpoint of preventing exposure of a worker to the drug, it is desirable to connect a syringe to the catheter via a closed-system connecting device, regardless of where the indwelling catheter is placed.

However, if male and female connectors constituting the connecting device are the same for every site in which a catheter is placed, a misconnection may occur, which is an accident in which, for example, a syringe storing a drug solution prepared for intravenous administration is mistakenly connected to a catheter placed in the bladder.

An object of the present invention is to prevent a misconnection between a male connector and a female connector of a connecting device constituted by the male connector and the female connector, using a simple method.

Means for Solving Problem

A connecting device of the present invention includes a male connector and a female connector that can be connected to and disconnected from each other. The male connector includes a rod-shaped male member, a hood surrounding the male member, and a first fitting structure provided on an inner circumferential surface of the hood. The female connector includes a female connector main body including a partition member in which a slit is formed, the partition member being made of an elastic material, a rotating cylinder provided on the female connector main body so as to be rotatable around the female connector main body, and a second fitting structure provided on an outer circumferential surface of the rotating cylinder. When the male connector is connected to the female connector, the male member passes through the slit of the partition member, the female connector is inserted into the hood, and the first fitting structure fits to the second fitting structure.

Effects of the Invention

According to the present invention, when the male connector is connected to the female connector, the first fitting structure fits to the second fitting structure. Therefore, it is possible to prevent a misconnection between the male connector and the female connector using a simple method of employing different configurations for the first fitting structure and the second fitting structure.

The second fitting structure is provided on the rotating cylinder that is rotatable around the female connector main body. Therefore, it is possible to rotate the male connector relative to the female connector main body in a state in which the first fitting structure is fitted to the second fitting structure (i.e., a state in which the male connector is connected to the female connector). Consequently, no rotational force is transmitted between the male connector and the female connector main body.

DESCRIPTION OF THE INVENTION

Figure 1A:
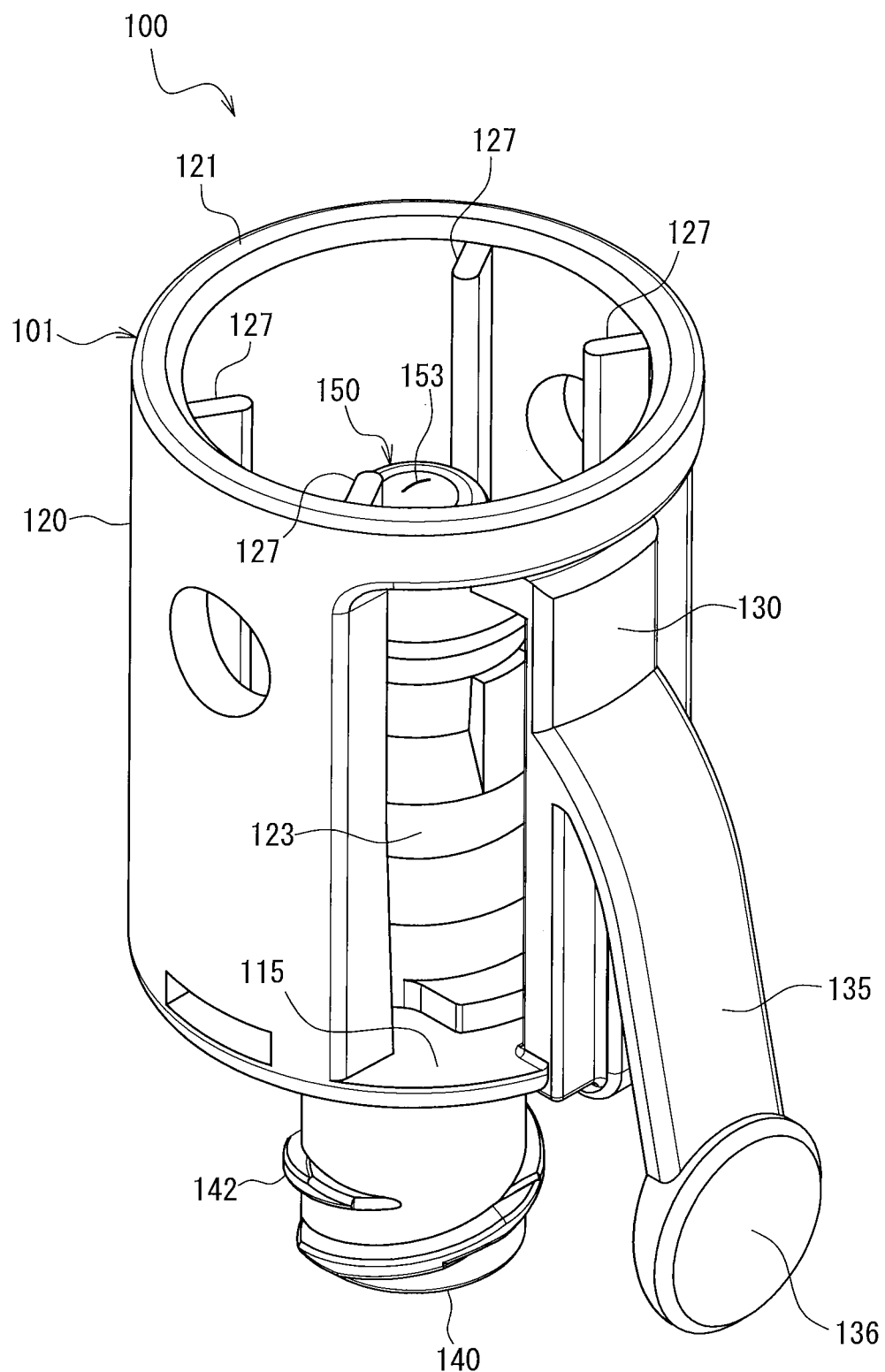
FIG. 1A is a perspective view of a male connector according to an embodiment of the present invention.

In an aspect of the connecting device of the present invention above, a configuration may be adopted in which the female connector cannot be inserted into the hood when the first fitting structure does not fit to the second fitting structure. This aspect is advantageous in preventing a liquid leakage from the connecting device to the outside when the first fitting structure does not fit to the second fitting structure.

In an aspect of the connecting device of the present invention above, the first fitting structure may be provided nearer to a distal end of the male connector than a distal end of the male member. This aspect is advantageous in preventing a liquid leakage from the connecting device to the outside when the first fitting structure does not fit to the second fitting structure.

In an aspect of the connecting device of the present invention above, the second fitting structure may be provided at or near a distal end of the female connector. This aspect is advantageous in preventing a liquid leakage from the connecting device to the outside when the first fitting structure does not fit to the second fitting structure.

In an aspect of the connecting device of the present invention above, in a process of connecting the male connector to the female connector and in a process of disconnecting the male connector from the female connector, the male connector may be movable in a longitudinal direction of the male member relative to the female connector, with the first fitting structure being fitted to the second fitting structure. This aspect is advantageous in improving the ease of operations for connecting and disconnecting the male connector to and from the female connector.

In an aspect of the connecting device of the present invention above, one of the first fitting structure and the second fitting structure may be a groove extending in a direction in which the male connector is connected to and disconnected from the female connector. Another one of the first fitting structure and the second fitting structure may be a projection that can fit into the groove. According to this aspect, the first fitting structure and the second fitting structure that can fit to each other when the male connector is connected to the female connector can be realized using a simple configuration.

In an aspect of the connecting device of the present invention above, in a state in which the male connector is connected to the female connector, the male connector may be rotatable relative to the female connector main body. According to this aspect, no rotational force is transmitted between the male connector and the female connector main body.

In an aspect of the connecting device of the present invention above, the male connector may further include a lock lever and a claw provided on the lock lever. The claw may be elastically displaceable in a direction away from the male member. When the male connector is connected to the female connector, the claw may engage with female connector. This aspect is advantageous in preventing unintentional disconnection of the male connector from the female connector.

When the male connector is connected to the female connector, the claw may engage with the rotating cylinder. According to this aspect, in a state in which the male connector is connected to the female connector, no rotational force is transmitted between the male connector and the female connector.

In an aspect of the connecting device of the present invention above, the male connector may further include a shield that is compressively deformable in a longitudinal direction of the male member. In a state in which the male connector is not connected to the female connector, the shield may close an opening of a flow channel provided in the male member. In a state in which the male connector is connected to the female connector, the shield may be compressively deformed in the longitudinal direction of the male member, and the male member may protrude from the shield. This aspect is advantageous in preventing a drug solution in the flow channel from leaking to the outside in a state in which the male connector is not connected to the female connector.

In an aspect of the connecting device of the present invention above, the male connector may further include, on a side opposite to the male member, a connecting cylinder that is disposed coaxially with the male member and is in communication with the male member. A male thread may be formed on an outer circumferential surface of the connecting cylinder. According to this aspect, the male connector can be connected to, for example, a barrel end of a syringe by means of thread-lock connection. Even if a rotational force is applied to the female connector main body, the rotational force does not loosen the screwing of the thread-lock connection.

Hereinafter, the present invention will be described in detail while showing a preferred embodiment thereof. However, it goes without saying that the present invention is not limited to the embodiment below. In the drawings that will be referred to in the following description, only the main constituent members of the embodiment of the present invention are shown in a simplified manner for the sake of convenience of description. Therefore, the present invention may include optional members that are not shown in the drawings below. Also, the members shown in the drawings below may be changed or omitted within the scope of the present invention. Identical members are denoted by identical reference numerals in different drawings.

1. Male Connector

Figure 1B:
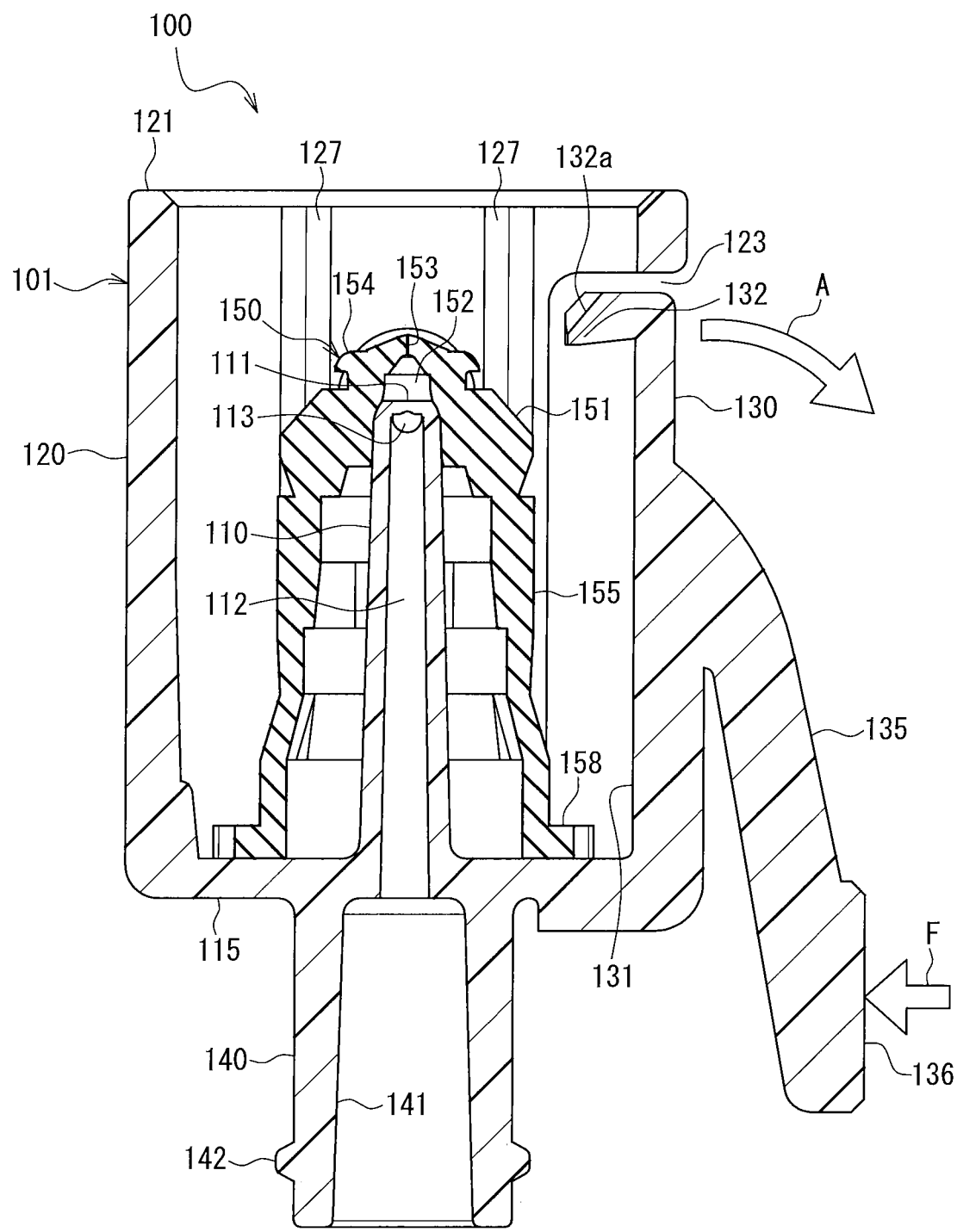
FIG. 1B is a cross-sectional view of the male connector according to the embodiment of the present invention, taken along a plane containing the central axis of the male connector.
Figure 1C:
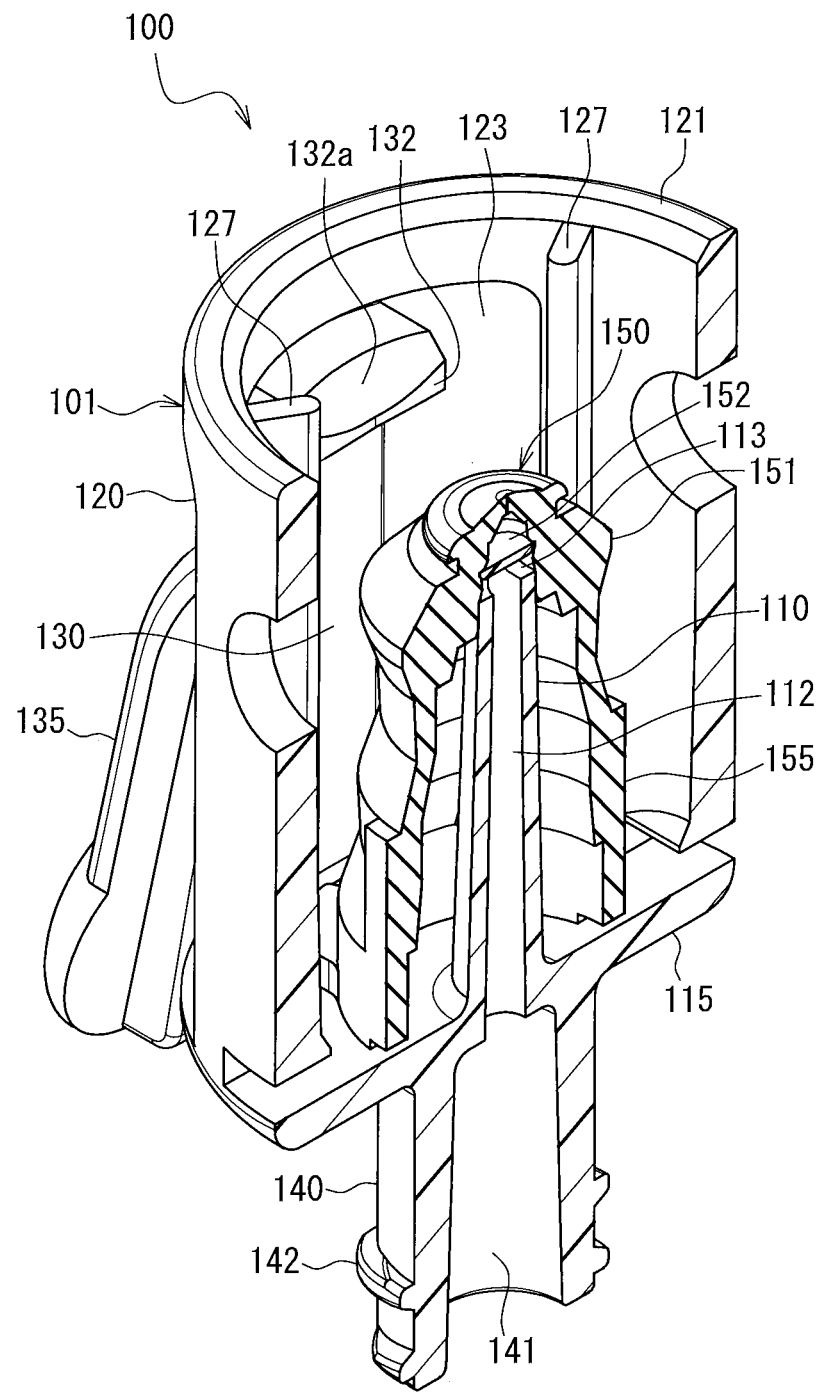
FIG. 1C is a cross-sectional perspective view of the male connector according to the embodiment of the present invention, taken along another plane containing the central axis of the male connector.
Figure 1D:
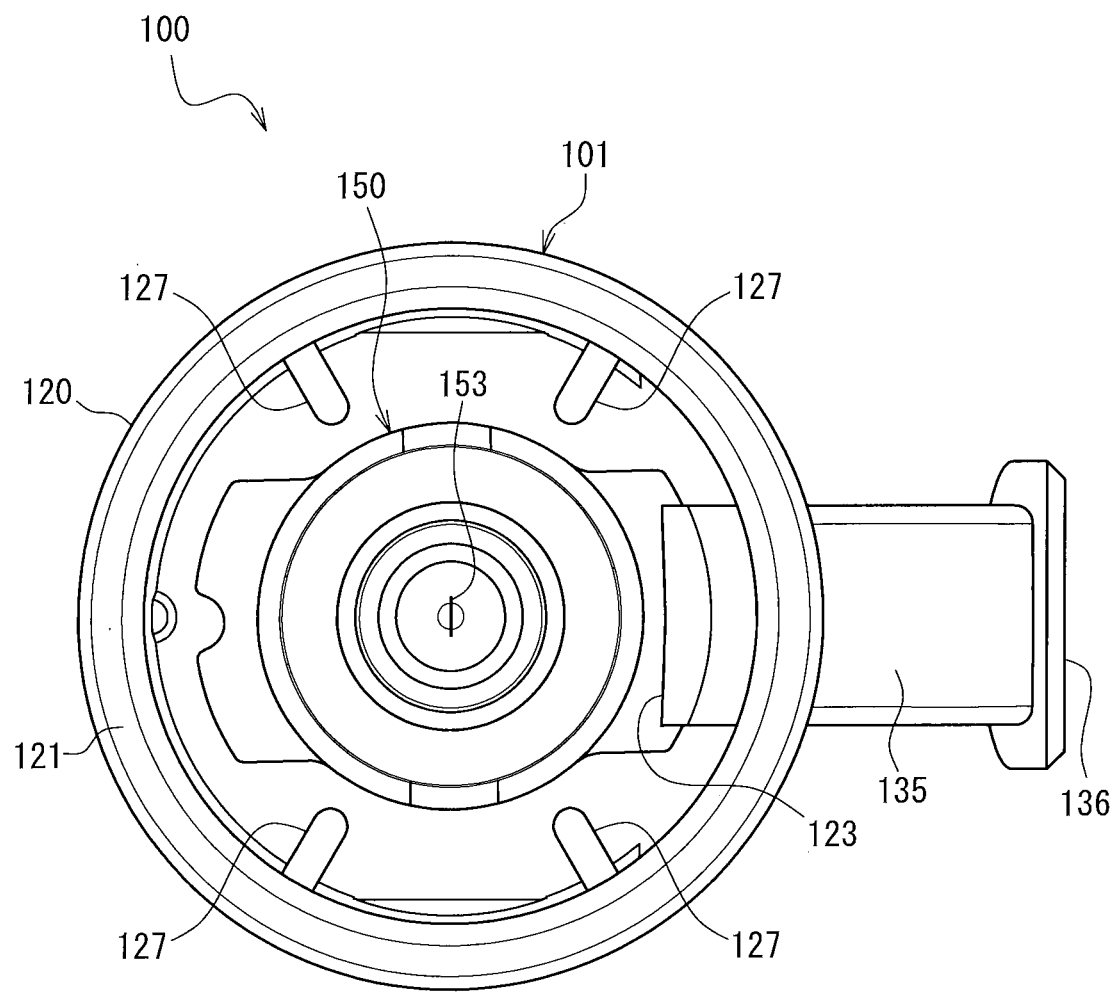
FIG. 1D is a plan view of the male connector according to the embodiment of the present invention.

A male connector 100 constituting a connecting device according to an embodiment of the present invention will be described. FIG. 1A is a perspective view of the male connector 100. FIG. 1B is a cross-sectional view of the male connector 100. FIG. 1C is a cross-sectional perspective view of the male connector 100. The cross section shown in FIG. 1B and the cross section shown in FIG. 1C are orthogonal to each other, where the central axis (not shown) of the male connector 100 is the line of intersection. FIG. 1D is a plan view of the male connector 100. The male connector 100 includes a male connector main body 101 and a shield 150. The male connector main body 101 includes a male member (male luer) 110, a hood 120, a lock lever 130, and a connecting cylinder 140.

For convenience of the following description, a longitudinal direction of the male member 110 is referred to as "vertical direction", a direction that is parallel to a plane perpendicular to the longitudinal direction of the male member 110 is referred to as "horizontal direction". However, the "vertical direction" and the "horizontal direction" do not mean the orientation of the male connector 100 when in actual use. A direction of rotation around the central axis of the male connector 100, which is also the central axis of the male member 110, is referred as "rotating direction" or "circumferential direction". Furthermore, a direction of a straight line orthogonal to the central axis is referred to as "radial direction". In the radial direction, the side nearer to the central axis is referred to as "inner side", and the side farther from the central axis is referred to as "outer side".

As shown in FIG. 1B, the male member 110 is a straight rod-shaped member. An outer circumferential surface (lateral surface) of the male member 110 is a tapered surface (conical surface) whose outer diameter gradually decreases toward a distal end 111 of the male member 110. However, the shape of the outer circumferential surface of the male member 110 is not limited to the above-described shape, and any shape can be chosen. For example, the outer circumferential surface of the male member 110 may constitute a cylindrical surface whose outer diameter is constant from a base end to the distal end 111 of the male member 110. Alternatively, the outer circumferential surface of the male member 110 may be formed of a combination of a tapered surface and a cylindrical surface, or may be formed of any desired curved surface.

A flow channel 112 is formed within the male member 110 and extends in the longitudinal direction of the male member 110. The flow channel 112 is not open in the distal end 111 of the male member 110. Two lateral holes 113 that are in communication with the flow channel 112 are formed in the outer circumferential surface of the male member 110 at respective positions near the distal end 111. Each lateral hole 113 extends in the radial direction of the male member 110 and is open in the outer circumferential surface of the male member 110. In the present embodiment, the two lateral holes 113 are arranged in a single straight line, but the number of lateral holes 113 is not necessarily required to be two and may also be one or three or more.

A flange 115 extends outward in the radial direction from the base end of the male member 110. The flange 115 is a substantially circular plate-like member. The hood 120 and the lock lever 130 extend toward the same side as the male member 110 from an outer circumferential edge of the flange 115.

The hood 120 has a hollow cylindrical shape. The hood 120 is coaxial with the male member 110, surrounds the male member 110, and is spaced apart from the male member 110 in the radial direction. The hood 120 is open upward (toward a side opposite to the flange 115) at a distal end 121 thereof. The distal end 121 of the hood 120 is located farther from the connecting cylinder 140 than the distal end 111 of the male member 110 in the vertical direction (or in other words, nearer to a distal end of the male connector 100 than the distal end 111).

An inner circumferential surface (surface that opposes the male member 110) of the hood 120 is a cylindrical surface whose inner diameter is constant in the longitudinal direction of the male member 110. The inner diameter of the inner circumferential surface of the hood 120 is slightly larger than the outer diameter of a female connector 200 (in particular, a rotating cylinder 250 thereof, see FIG. 2A, which will be described later) to which the male connector 100 is to be connected. Four ribs (projections) 127 protrude from the inner circumferential surface of the hood 120 toward the male member 110. The four ribs 127 are spaced apart from each other in the circumferential direction. The ribs 127 extend parallel to the longitudinal direction of the male member 110, from the distal end 121, or a position near the distal end 121, of the hood 120 to the flange 115. Upper ends of the ribs 127 are located farther from the connecting cylinder 140 than the distal end 111 of the male member 110 in the vertical direction (or in other words, nearer to the distal end of the male connector 100 than the distal end 111).

The lock lever 130 opposes the male member 110 in the radial direction. The lock lever 130 has an elongated thin plate-like shape (strip-like shape), and its longitudinal direction is substantially parallel to the longitudinal direction of the male member 110.

The lock lever 130 has a cantilever structure, with its fixed end (base end) being fixed to the flange 115. A claw 132 protruding toward the male member 10 is provided at or near a free end (distal end) of the lock lever 130. The claw 132 has an inclined surface 132a above (on the side opposite to the flange 115) its protruding end (a portion closest to the male member 110). The inclined surface 132a is inclined so as to be closer to the flange 115 toward the protruding end of the claw 132. The claw 132 protrudes toward the male member 110 than the inner circumferential surface of the hood 120.

An operating arm 135 protrudes outward (toward a side away from the male member 110) from a surface of the lock lever 130 that is located on the side opposite to the male member 110. The operating arm 135 extends beyond the fixed end of the lock lever 130 (or the flange 115) toward the connecting cylinder 140 from a position between the fixed end and the free end of the lock lever 130 while being spaced apart from the lock lever 130. An operating portion 136 is provided at a distal end of the operating arm 135. The operating arm 135 has a mechanical strength that is high enough for the operating arm 135 to be considered as a substantially rigid body.

The lock lever 130 can elastically bend and deform and can thus swing in a plane containing the central axis of the male member 110. For example, when a force F acting inward in the radial direction is applied to the operating portion 136, the claw 132 moves in the direction of arrow A (outward in the radial direction) so as to move away from the male member 110 substantially in the radial direction. A portion of the lock lever 130 that is located between the fixed end and the position to which the operating arm 135 is connected is an elastic portion 131. When the force F is applied to the operating portion 136, mainly the elastic portion 131 elastically bends and deforms.

An opening 123 penetrating the hood 120 in the radial direction is formed in the hood 120. The opening 123 has an inverted substantially "U" shape. The opening 123 does not reach the distal end 121 of the hood 120. The opening 123 allows the lock lever 130 to be spaced apart from the hood 120 so that the lock lever 130 can swing. The lock lever 130 is disposed within the opening 123 while extending substantially along the cylindrical surface formed by the hood 120.

The connecting cylinder 140 extends downward (toward a side opposite to the male member 110) from the flange 115. The connecting cylinder 140 has a substantially cylindrical shape that is coaxial with the male member 110, and is in communication with the flow channel 112 of the male member 110. An inner circumferential surface 141 of the connecting cylinder 140 constitutes a female tapered surface (e.g., a 6% tapered surface) whose inner diameter increases as the distance from the flange 115 increases. A male thread 142 is formed on an outer circumferential surface of the connecting cylinder 140. The connecting cylinder 140 and the male thread 142 may comply with ISO 594-2, for example. The connecting cylinder 140 including the inner circumferential surface 141 and the male thread 142 constitutes a base end portion of the male connector 100.

It is preferable that the male connector main body 101 is made of a hard material. Specifically, a resin material such as polyacetal, polycarbonate, polystyrene, polyamide, polypropylene, or rigid polyvinyl chloride can be used. The entire male connector main body 101 can be integrally produced as a single component through injection molding or the like using such a resin material.

The shield 150 is disposed inside the hood 120 so as to cover the male member 110. The shield 150 includes a head portion 151, a circumferential wall 155, and a base portion 158 in this order. The shield 150 is made of an elastic (or flexible) soft material (so-called elastomer) so that it can be relatively easily deformed by an external force and immediately recover to a state before deformation (initial state) when the external force is removed. Examples of soft materials that can be used include, but are not limited to, soft polyvinyl chloride, thermoplastic elastomers (e.g., styrene-based elastomers, olefin-based elastomers, polyurethane-based elastomers, etc.), and rubbers (e.g., isoprene rubber, silicone rubber, butyl rubber, etc.). The entire shield 150 can be integrally produced as a single component using such a material.

The circumferential wall 155 has a hollow cylindrical shape as a whole. When a compressive force acting in the vertical direction is applied to the shield 150, the circumferential wall 155 is elastically compressively deformed such that its vertical length is reduced (see FIG. 4B, which will be described later), and when released from the compressive force, the circumferential wall 155 immediately returns to the initial state (see Patent Document 1, for example).

The head portion 151 has an inner cavity 152 that is in communication with an inner space of the circumferential wall 155. It is preferable that an inner circumferential surface of the inner cavity 152 has a shape that conforms to the outer circumferential surface of the male member 110 so as to come into intimate contact with the outer circumferential surface of the male member 110. In the present embodiment, the inner circumferential surface of the inner cavity 152 constitutes a cylindrical surface whose inner diameter is constant in the vertical direction. A slit 153 penetrating the head portion 151 in the vertical direction is formed at the innermost portion of the inner cavity 152. The slit 153 is a straight line-shaped cut portion having a "-" (minus sign) shape in a plan view. A conical surface-shaped (or a mushroom- or umbrella-shaped) convex portion 154 protrudes upward from an upper surface of the head portion 151. The slit 153 passes through the central apex of the convex portion 154.

The base portion 158 protrudes outward in the radial direction from a lower end of the circumferential wall 155. The base portion 158 is placed on the flange 115, and an annular fixing ring (not shown) is put on the base portion 158. The fixing ring is locked to the male connector main body 101. In this manner, the shield 150 is fixed to the male connector main body 101. However, the method for fixing the shield 150 to the male connector main body 101 is not limited to this method, and any methods can be used. The configuration of the base portion 158 may be changed as appropriate depending on the fixing method.

The distal end 111 and its neighboring portion of the male member 110 are inserted into the inner cavity 152 of the shield 150. The inner circumferential surface of the inner cavity 152 is expanded in diameter by the male member 110 and is in intimate contact with the male member 110. The distal end 111 of the male member 110 is spaced apart from the slit 153 of the shield 150 in the vertical direction. A liquid-tight space defined by the distal end 111 and the inner circumferential surface of the inner cavity 152 is formed. As shown in FIG. 1C, the lateral holes 113 of the male member 110 are closed by the inner circumferential surface of the inner cavity 152 in a liquid-tight manner.

FIGS. 1A to 1D show the male connector 100 in the initial state. In the initial state, the shield 150 is not substantially compressively deformed in the vertical direction, the slit 153 is closed in a liquid-tight manner, and the lock lever 130 is not bent and deformed.

2. Female Connector

Figure 2A:
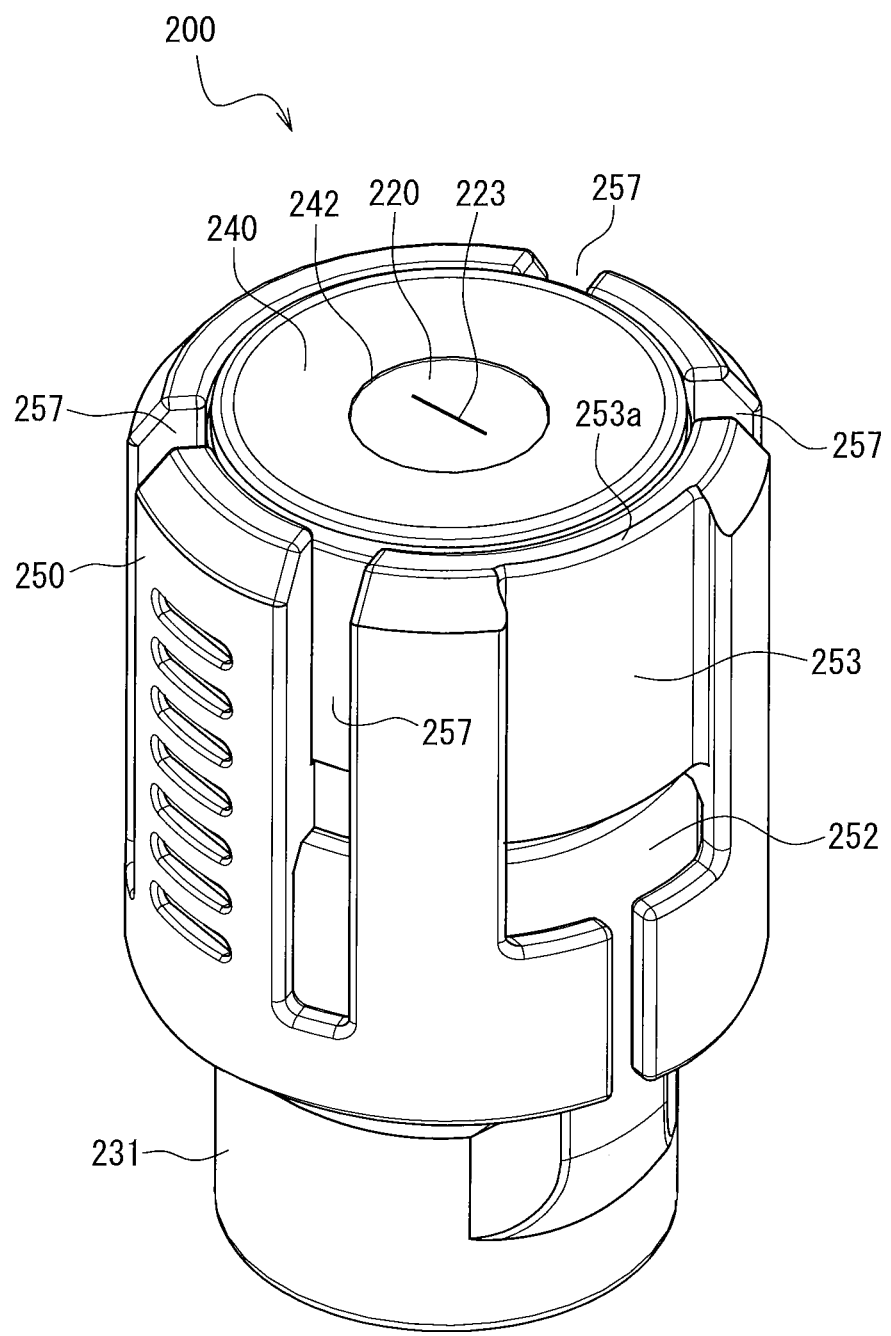
FIG. 2A is a perspective view of a female connector according to the embodiment of the present invention.
Figure 2B:
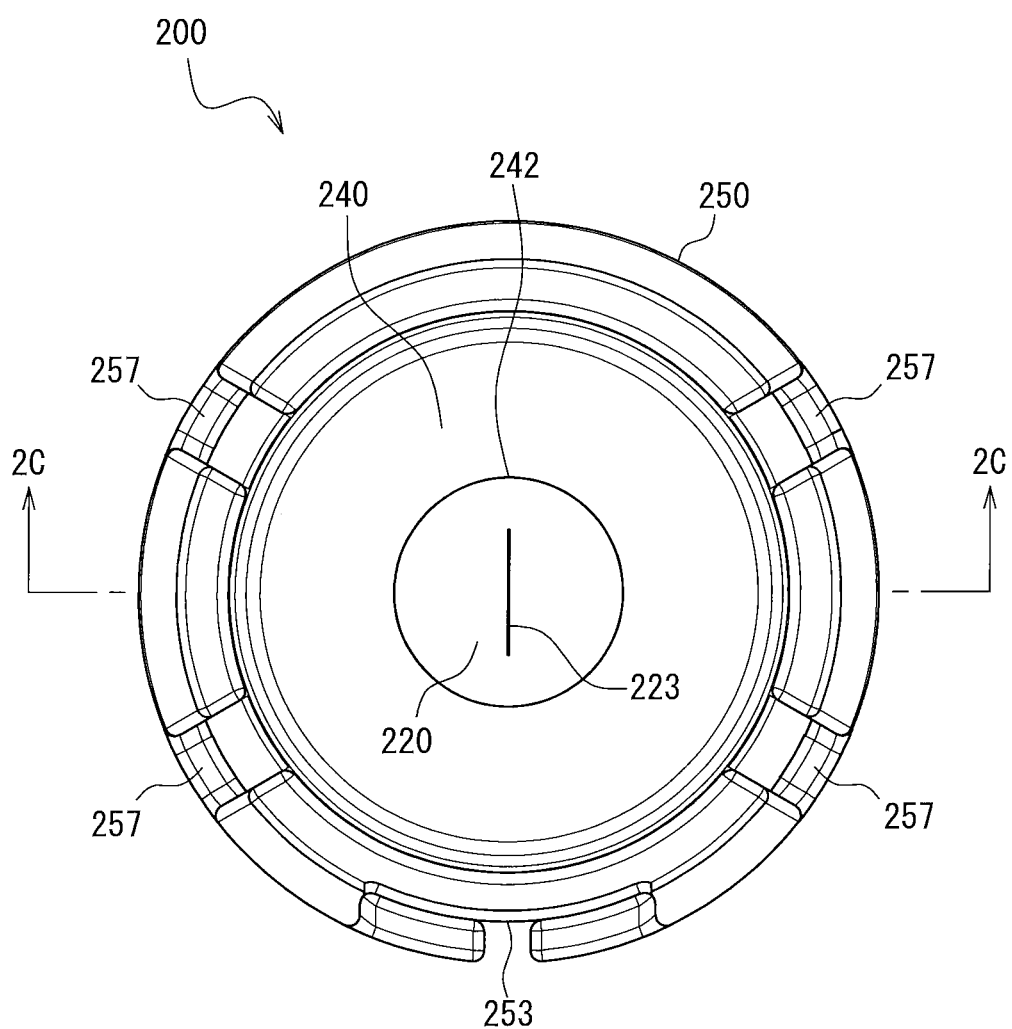
FIG. 2B is a plan view of the female connector according to the embodiment of the present invention.
Figure 2C:
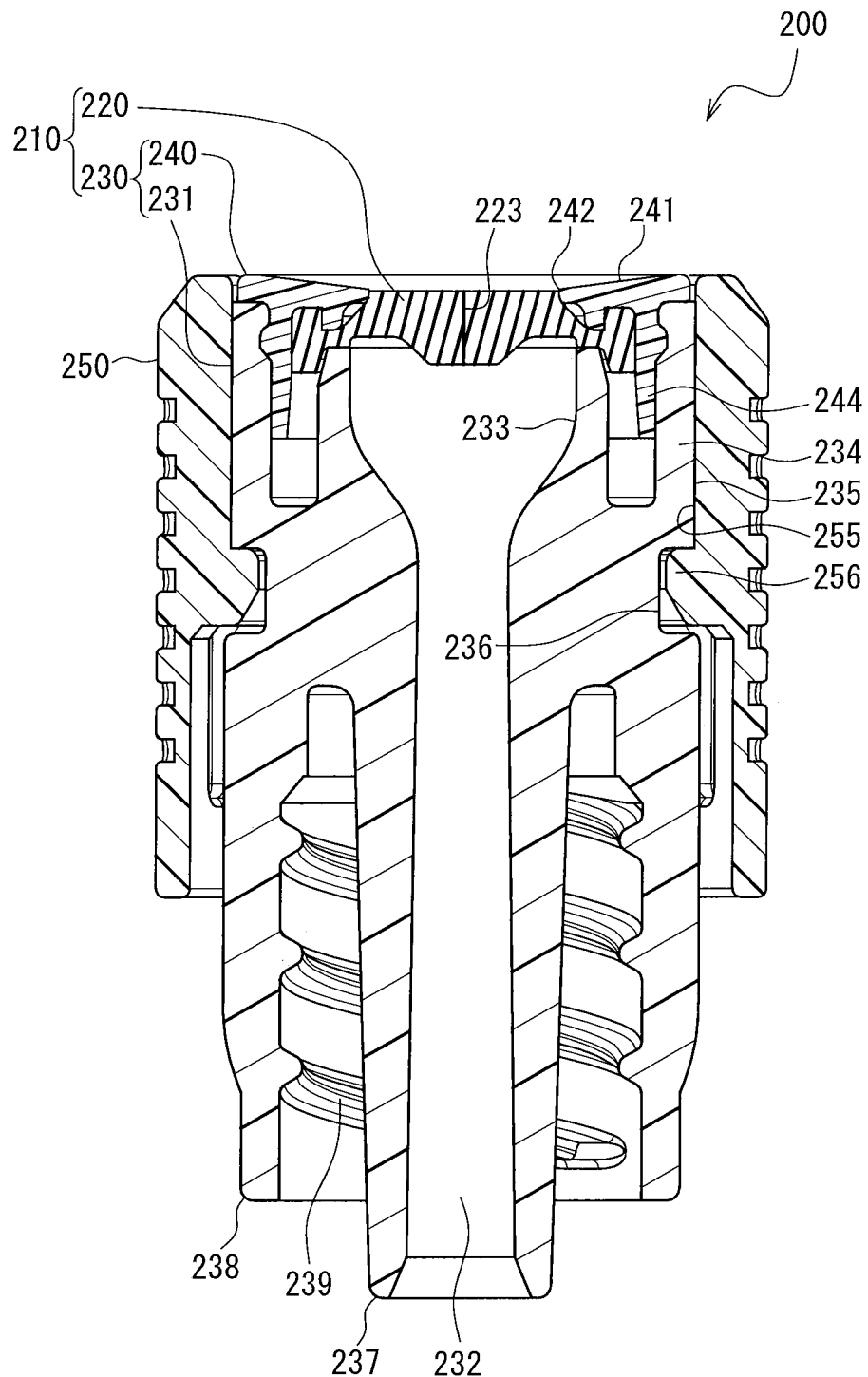
FIG. 2C is a cross-sectional view of the female connector according to the embodiment of the present invention, taken along a plane containing line 2C-2C in FIG. 2B and viewed in the direction of the arrows.
Figure 2D:
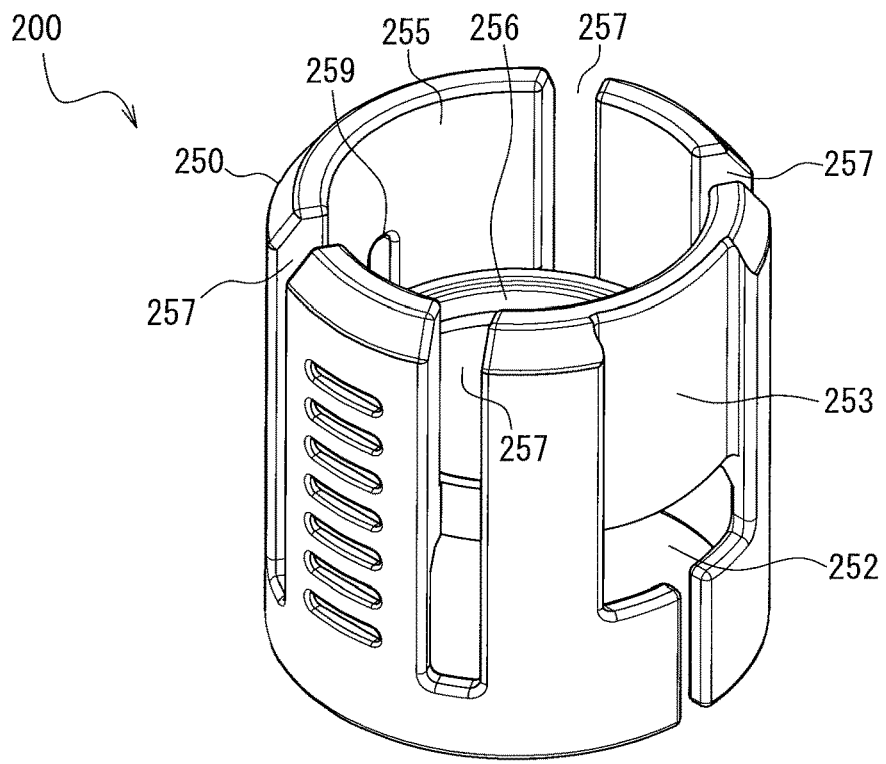
FIG. 2D is an exploded perspective view of the female connector according to the embodiment of the present invention.
Figure 2D:
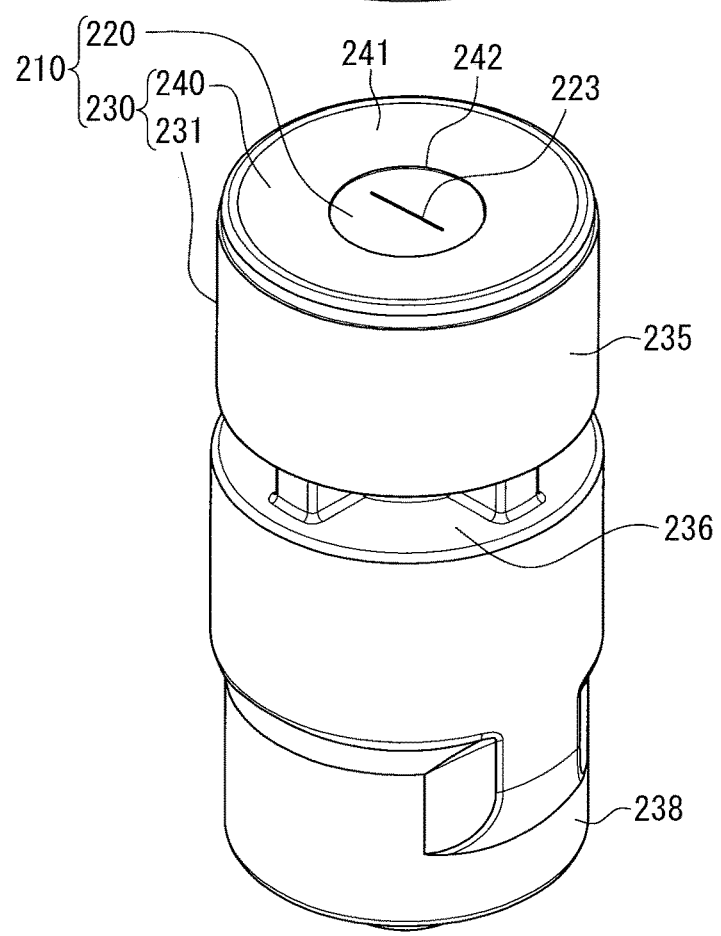

The female connector 200 constituting the connecting device according to the embodiment of the present invention will be described. FIG. 2A is a perspective view of the female connector 200. FIG. 2B is a plan view of the female connector 200. FIG. 2C is a cross-sectional view of the female connector 200. The cross section shown in FIG. 2C is taken along line 2C-2C in FIG. 2B, and this cross section contains the central axis (not shown) of the female connector 200. FIG. 2D is an exploded perspective view of the female connector 200. For convenience of the following description, a direction that is parallel to the central axis of the female connector 200 is referred to as "vertical direction", and a direction that is parallel to a plane perpendicular to the central axis of the female member 200 is referred to as "horizontal direction". However, the "vertical direction" and the "horizontal direction" do not mean the orientation of the female connector 200 when in actual use. A direction of rotation around the central axis is referred to as "rotating direction" or "circumferential direction". Furthermore, a direction of a straight line orthogonal to the central axis of the female connector 200 is referred to as "radial direction". In the radial direction, the side nearer to the central axis is referred to as "inner side", and the side farther from the central axis is referred to as "outer side".

As shown in FIG. 2D, the female connector 200 includes a female connector main body 210 and a rotating cylinder 250. As shown in FIG. 2C, the female connector main body 210 includes a partition member (hereinafter referred to as "septum") 220 and a housing 230. The housing 230 includes a housing base 231 and a cap 240.

The septum 220 has a circular thin plate-like shape. A straight-line shaped slit (cut) 223 penetrating the septum 220 in its thickness direction is formed at the center of the septum 220. The septum 220 is made of an elastic (or flexible) soft material (so-called elastomer) so that it can be relatively easily deformed by an external force and immediately return to a state before deformation (initial state) when the external force is removed. Examples of soft materials that can be used include, but are not limited to, soft polyvinyl chloride, thermoplastic elastomers (e.g., styrene-based elastomers, olefin-based elastomers, polyurethane-based elastomers, etc.), and rubbers (e.g., isoprene rubber, silicone rubber, butyl rubber, etc.). The entire septum 220 can be integrally produced as a single component using such a material. FIGS. 2A to 2D show the female connector 200 in the initial state. In the initial state, the slit 223 is closed in a liquid-tight manner. The female connector 200 including the septum 220 in which the slit 223 is formed is generally called a needleless port.

The housing base 231 has a substantially hollow cylindrical shape as a whole, and a flow channel 232 penetrates the housing base 231 along the central axis. An upper section of the housing base 231 has a double cylinder structure consisting of an inner cylinder 233 that defines the flow channel 232 and an outer cylinder (first outer cylinder) 234 that is spaced apart from the inner cylinder 233 in a radially outward direction. The inner cylinder 233 and the outer cylinder 234 both have a substantially cylindrical shape and are arranged coaxially. The septum 220 is placed on a distal end of the inner cylinder 233 so as to close the flow channel 232. The cap 240 is put on the septum 220. A locking cylinder 244 extending from a top plate 241 of the cap 240 is inserted between the inner cylinder 233 and the outer cylinder 234 and fixed to the outer cylinder 234. Thus, the septum 220 is sandwiched between the housing base 231 (in particular, the inner cylinder 233 thereof) and the cap 240 (in particular, the top plate 241 thereof) in the vertical direction. A circular opening 242 is formed at the center of the circular top plate 241 of the cap 240. A region of the septum 220 where the slit 223 is formed is exposed through the opening 242 (see FIG. 2A).

A lower section of the housing base 231 includes a hollow male luer 237 that defines the flow channel 232 and an outer cylinder (second outer cylinder) 238 that surrounds the male luer 237. An outer circumferential surface of the male luer 237 constitutes a male tapered surface (e.g., a 6% tapered surface) whose outer diameter decreases as the distance to a distal end of the male luer 237 decreases (that is, as the distance from the septum 220 increases). The outer cylinder 238 has a substantially cylindrical shape and is disposed coaxially with the male luer 237 while being spaced apart from the male luer 237 in the radial direction. A female thread 239 is formed on an inner circumferential surface of the outer cylinder 238. The male luer 237, the outer cylinder 238, and the female thread 239 may comply with ISO 594-2, for example. Note that the configuration of the lower section of the housing base 231 is not limited to this configuration, and any configuration may be adopted. The lower section of the housing base 231 constitutes a base end portion of the female connector 200 (female connector main body 210).

As shown in FIG. 2D, an outer circumferential surface of the outer cylinder 234 includes a cylindrical surface 235. An annular groove 236 is formed below and adjacent to the cylindrical surface 235. The annular groove 236 is continuous in the circumferential direction over the entire circumference of the housing base 231.

It is preferable that the housing base 231 and the cap 240 are made of a hard material. Specifically, a resin material such as polyacetal, polycarbonate, polystyrene, polyamide, polypropylene, or rigid polyvinyl chloride can be used. The entire housing base 231 and the entire cap 240 can each be integrally produced as a single component through injection molding or the like using such a resin material.

The rotating cylinder 250 has a hollow substantially cylindrical shape. An annular projection 256 protrudes inward from an inner circumferential surface of the rotating cylinder 250. The annular projection 256 extends in the circumferential direction. The inner circumferential surface of the rotating cylinder 250 includes a cylindrical surface 255 above and adjacent to the annular projection 256. The inner diameter of the rotating cylinder 250 at the position of the annular projection 256 is smaller than the outer diameter of the cylindrical surface 235 of the female connector main body 210. The inner diameter of the cylindrical surface 255 is slightly larger than the outer diameter of the cylindrical surface 235.

Four grooves (or slits) 257 are formed in an outer circumferential surface of the rotating cylinder 250. The four grooves 257 are spaced apart from each other in the circumferential direction. The grooves 257 extend downward from a distal end of the rotating cylinder 250 (upper end of the rotating cylinder 250 in FIG. 2D), are parallel to the central axis of the rotating cylinder 250, and have a predetermined length.

An opening 252 penetrating the rotating cylinder 250 in the radial direction is formed in the rotating cylinder 250. The opening 252 is disposed in a region where no grooves 257 are formed. The opening 252 has a substantially rectangular opening shape. A guide groove 253 is formed in the outer circumferential surface of the rotating cylinder 250. The guide groove 253 extends from the upper end of the rotating cylinder 250 to the opening 252. The width (circumferential length) of the guide groove 253 is constant in the vertical direction and is equal to the circumferential length of the opening 252.

The female connector main body 210 is inserted into the rotating cylinder 250 from below the rotating cylinder 250 (see FIG. 2D). A slit 259 (see FIGS. 2D and 3B) penetrating the rotating cylinder 250 in the radial direction extends from a lower end of the rotating cylinder 250 to a position higher than the annular projection 256. The slit 259 makes it easy for the rotating cylinder 250 to expand in diameter when the annular projection 256 passes over the cylindrical surface 235.

As shown in FIG. 2C, when the rotating cylinder 250 is attached to the female connector main body 210, the annular projection 256 of the rotating cylinder 250 fits into the annular groove 236 of the female connector main body 210. The rotating cylinder 250 is positioned in the vertical direction relative to the female connector main body 210. The distal end of the rotating cylinder 250 and the top plate 241 of the cap 240 are substantially coplanar with each other.

Once the annular projection 256 fits into the annular groove 236, it is difficult to separate the rotating cylinder 250 from the female connector main body 210. In a state in which the annular projection 256 is fitted in the annular groove 236, the rotating cylinder 250 can freely rotate around the female connector main body 210. The cylindrical surface 255 of the rotating cylinder 250 faces the cylindrical surface 235 of the female connector main body 210 in the radial direction, and slides on the cylindrical surface 235.

It is preferable that the rotating cylinder 250 is made of a hard material. Specifically, resin materials such as polyethylene, polypropylene, polycarbonate, styrene-ethylene, polyethylene terephthalate, polybutylene terephthalate, and a butylene-styrene block copolymer can be used. When consideration is given to the ease of deformation of the rotating cylinder 250 during attachment of the rotating cylinder 250 to the female connector main body 210 and the durability thereof against engagement of the claw 132 of the lock lever 130 with the rotating cylinder 250 (see FIG. 4B), it is preferable that the material of the rotating cylinder 250 has toughness, and in view of this, a polyolefin-based resin such as polyethylene or polypropylene is preferable. The entire rotating cylinder 250 can be integrally produced as a single component through injection molding or the like using such a resin material.

3. Connecting Device

A connecting device 1 according to the embodiment of the present invention is constituted by the male connector 100 (see FIGS. 1A to 1D) and the female connector 200 (see FIGS. 2A to 2D). The connecting device 1 can be used to administer a drug solution to a patient. A method of using the connecting device 1 will be described below.

Figure 3A:
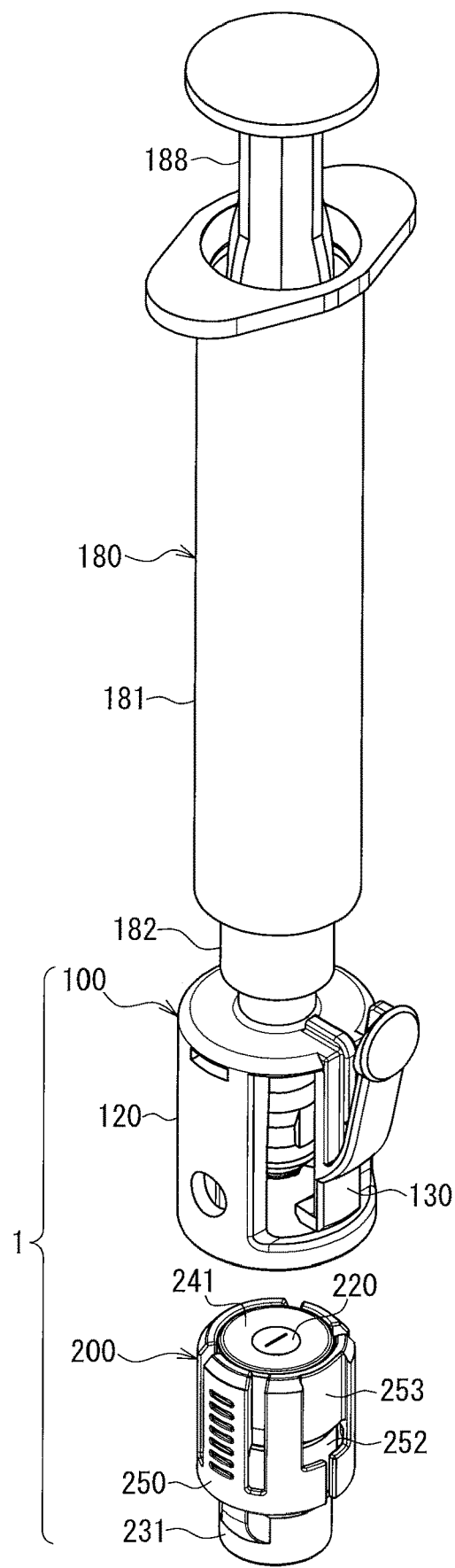
FIG. 3A is a perspective view illustrating a method of using a connecting device according to the embodiment of the present invention and shows a state before the male connector is connected to the female connector.
Figure 3B:
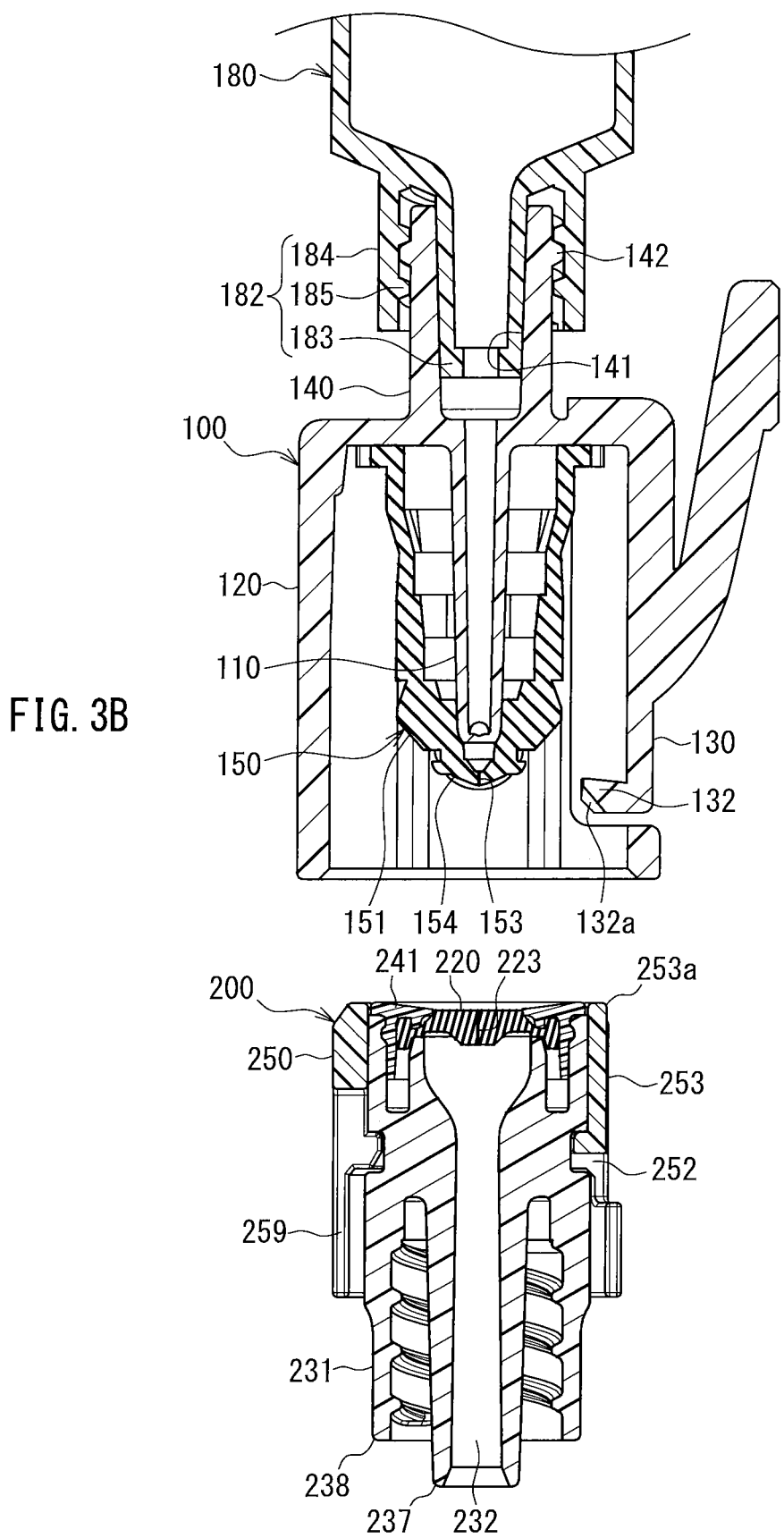
FIG. 3B is a cross-sectional view of main portions in FIG. 3A.

FIG. 3A is a perspective view illustrating a method of using the connecting device 1. FIG. 3B is a cross-sectional view of main portions in FIG. 3A. The cross section shown in FIG. 3B is taken along the central axis (not shown) shared by the male connector 100 and the female connector 200 and the lock lever 130.

The male connector 100 is connected to a barrel end 182 of an outer barrel 181 of a syringe 180. As shown in FIG. 3B, the barrel end 182 includes a male luer 183 and a lock cylinder 184 surrounding the male luer 183. The male luer 183 is in communication with an inner cavity of the syringe 180 (or the outer barrel 181). An outer circumferential surface of the male luer 183 constitutes a male tapered surface (e.g., a 6% tapered surface) whose outer diameter gradually decreases toward its distal end. A female thread 185 is formed on an inner circumferential surface of the lock cylinder 184. The connecting cylinder 140 of the male connector 100 is inserted into a gap between the male luer 183 and the lock cylinder 184. The inner circumferential surface (female tapered surface) 141 of the connecting cylinder 140 and the male tapered surface of the male luer 183 are taper-fitted to each other, and the male thread 142 of the connecting cylinder 140 is screwed into the female thread 185 of the lock cylinder 184. The connecting cylinder 140 and the barrel end 182 are securely fitted to each other by means of so-called thread-lock connection. The connection between the connecting cylinder 140 and the barrel end 182 may comply with ISO 594-2. A drug solution is stored in the syringe 180.

The female connector 200 is provided at an upstream end of a catheter (not shown). The catheter is inserted into a patient, and the distal end of the catheter reaches a desired site (e.g., a vein, bladder, medullary cavity, or gastrointestinal tract). In the present embodiment, the base end portion (the male luer 237 and the outer cylinder 238) of the female connector 200 (the female connector main body 210) is connected to a connector (not shown) provided at the upstream end of the catheter. The connector of the catheter has substantially the same configuration as the connecting cylinder 140, and this connector and the female connector 200 are connected to each other in compliance with ISO 594-2. However, the configuration of the connection portion between the catheter and the female connector 200 is not limited to that of the present embodiment, and may be changed as desired. The base end portion of the female connector 200 may be changed as appropriate depending on the configuration of the connector provided at the upstream end of the catheter.

As shown in FIG. 3A, the distal end of the male connector 100 is placed coaxially with and opposite to the distal end of the female connector 200. A worker can hold the outer barrel 181 or the hood 120 with one hand (e.g., right hand) and the rotating cylinder 250 with the other hand (e.g., left hand). The male connector 100 and the rotating cylinder 250 are aligned with each other in the circumferential direction such that the circumferential position of the guide groove 253 and the opening 252 of the rotating cylinder 250 coincides with that of the lock lever 130. Since the rotating cylinder 250 can freely rotate relative to the female connector main body 210, the catheter connected to the female connector main body 200 does not twist even when the rotating cylinder 250 is rotated. Therefore, it is easy to align the male connector 100 and the rotating cylinder 250 with each other in the circumferential direction.

Then, the female connector 200 is inserted and pushed into the hood 120 of the male connector 100.

As can be seen from FIG. 3B, the female connector 200 (in particular, the top plate 241 and the septum 220) collides with the convex portion 154 of the shield 150 and moves the head portion 151 toward the syringe 180. The male member 110 passes through the slit 153 of the shield 150 and further enters the slit 223 of the septum 220. In parallel with this, a distal end 253a (see FIG. 2A) of the guide groove 253 of the rotating cylinder 250 comes into contact with the inclined surface 132a (see FIGS. 1B and 1C) of the claw 132 of the lock lever 130. While sliding on the inclined surface 132a, the distal end 253a causes the lock lever 130 to elastically bend and deform in a direction (direction indicated by arrow A in FIG. 1B) in which the claw 132 moves away from the male member 110. Then, the claw 132 slide on the guide groove 253. When the claw 132 finishes passing through the guide groove 253, the lock lever 130 elastically recovers, and the claw 132 fits into the opening 252.

Figure 4A:
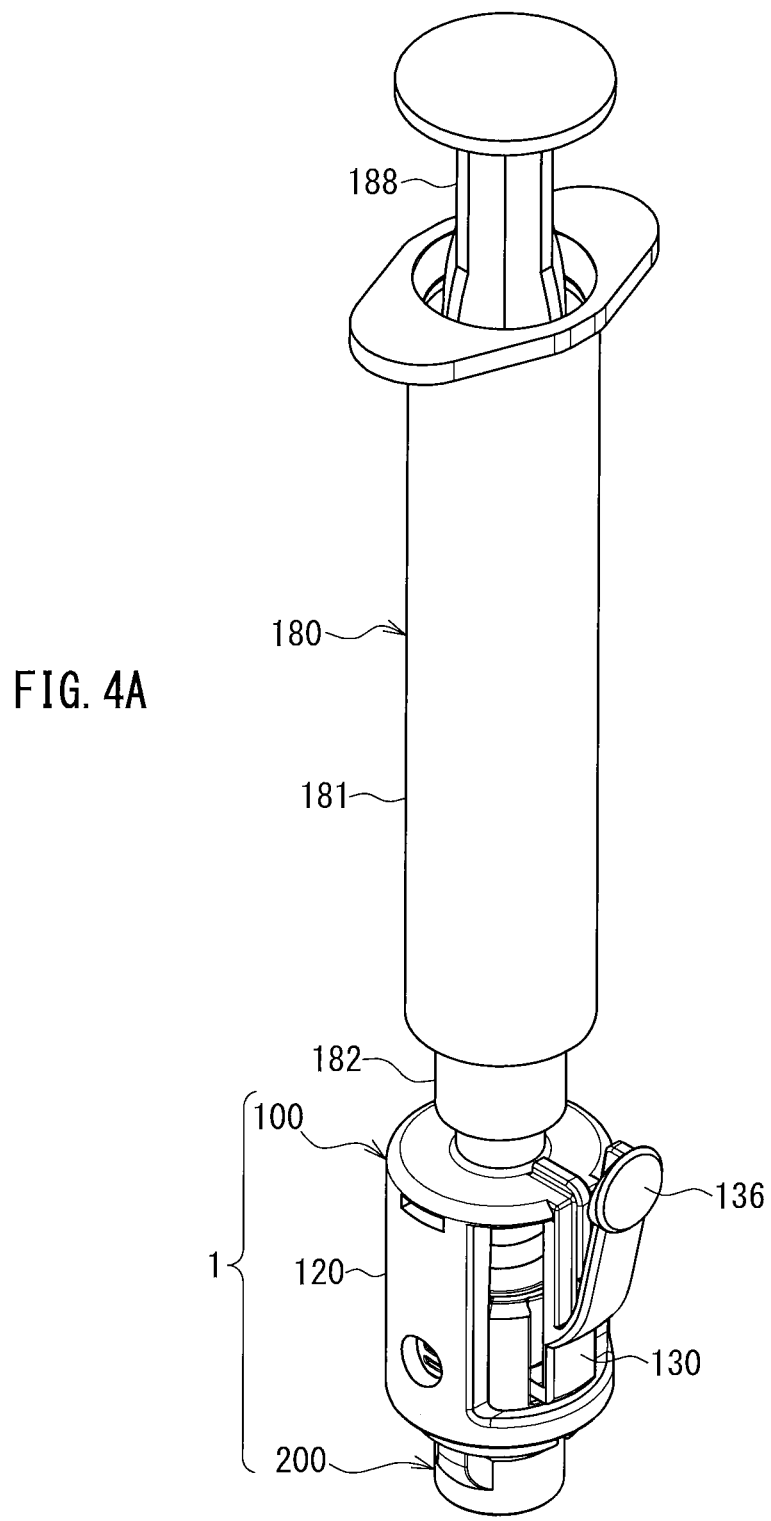
FIG. 4A is a perspective view illustrating the method of using the connecting device according to the embodiment of the present invention and shows a state in which the male connector is connected to the female connector.
Figure 4B:
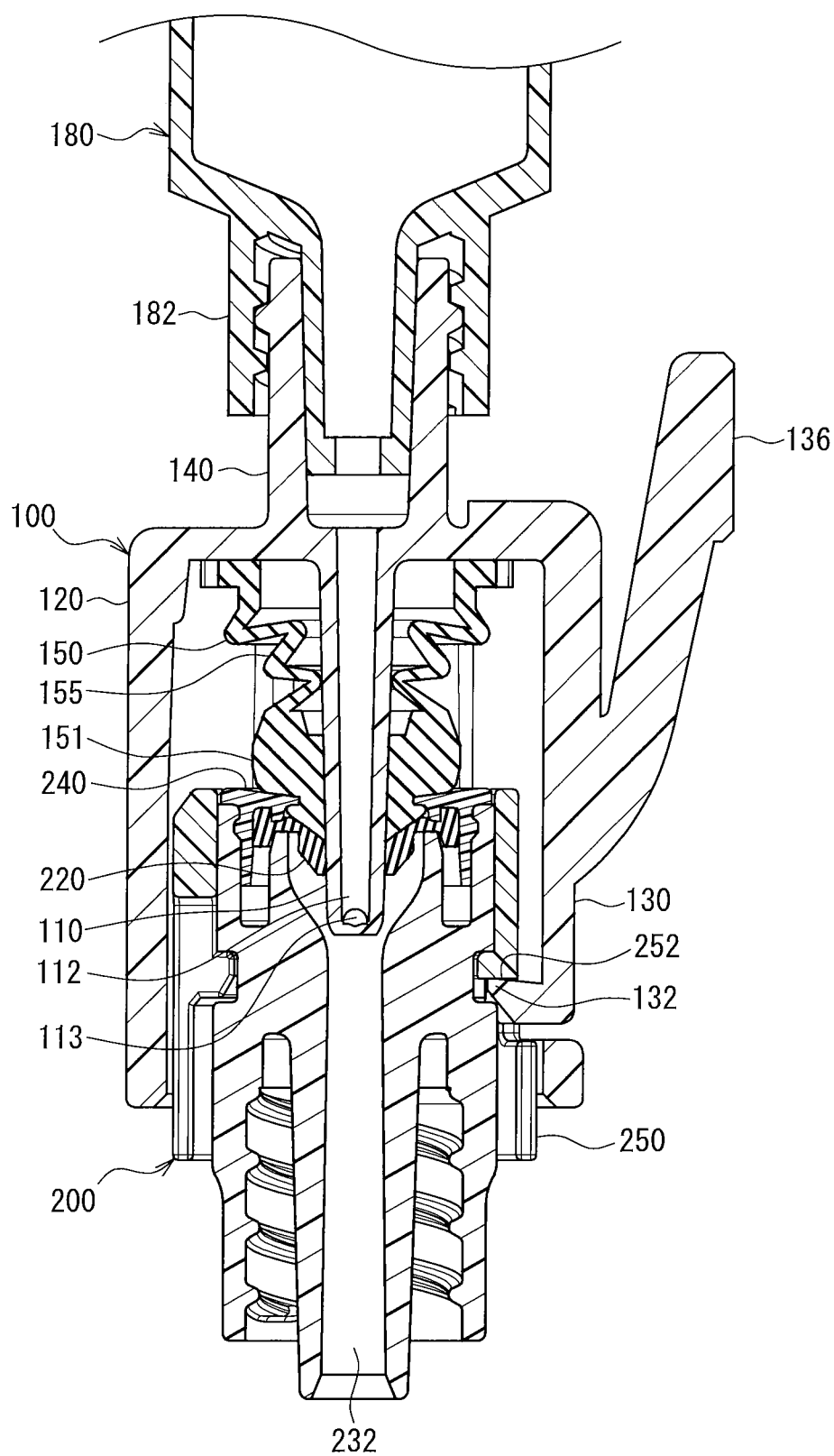
FIG. 4B is a cross-sectional view of main portions in FIG. 4A.

FIG. 4A is a perspective view of the connecting device 1 in which the male connector 100 is connected to the female connector 200. FIG. 4B is a cross-sectional view of main portions in FIG. 4A. The male member 110 passes through the slit 153 (see FIG. 1B) of the shield 150 and the slit 223 (see FIG. 2C) of the septum 220 in this order. The convex portion 154 (see FIG. 1B) of the shield 150 enters the inside of the opening 242 (see FIG. 2C) of the cap 240. The septum 220 is significantly deformed into the flow channel 232 by the male member 110 and the shield 150. The lateral holes 113 of the male member 110 are exposed in the flow channel 232. The flow channel 112 of the male member 110 and the flow channel 232 of the female connector 200 are in communication with each other. The shield 150 receives a compressive force acting in the vertical direction, and the circumferential wall 155, in particular, is compressively deformed such that the vertical length of the shield 150 is reduced. The lock lever 130 has recovered to substantially the same state as the initial state. The claw 132 of the lock lever 130 is engaged with the rotating cylinder 250 (locked state). Even if a pulling force is applied between the male connector 100 and the female connector 200, the male connector 100 cannot be disconnected from the female connector 200.

The four ribs 127 (see FIG. 1D) of the male connector 100 and the four grooves 257 (see FIG. 2B) of the rotating cylinder 250 are arranged such that, when the lock lever 130 (in particular, the claw 132 thereof) is aligned with the guide groove 253 and the opening 252 of the rotating cylinder 250 in the circumferential direction as shown in FIG. 3A, the circumferential positions of the four ribs 127 coincide with the circumferential positions of the four grooves 257. Therefore, although not shown, the ribs 127 fit into the grooves 257 when the male connector 100 is connected to the female connector 200 (see FIGS. 4A and 4B).

In the state in which the male connector 100 is connected to the female connector 200 (see FIGS. 4A and 4B), a plunger 188 of the syringe 180 is pushed in to administer the drug solution in the syringe 180 to the patient through the male connector 100 and the female connector 200.

To disconnect the male connector 100 from the female connector 200, the operating portion 136 of the lock lever 130 is pushed inward in the radial direction (direction indicated by arrow F in FIG. 1B). The lock lever 130 elastically bends and deforms, and the claw 132 moves outward in the radial direction. The claw 132 comes out of the opening 252, and the engagement of the claw 132 with the rotating cylinder 250 is cancelled (unlocked state). In this state, if the male connector 100 and the female connector 200 are pulled away from each other, the male connector 100 can be disconnected from the female connector 200. The septum 220 elastically recovers as soon as the male member 110 is removed therefrom, the slit 223 is closed in a liquid-tight manner. The shield 150 expands due to the elastic recovery force it has. The male member 110 is accommodated in the shield 150, and the lateral holes 113 are closed by the shield 150. The slit 153 is closed in a liquid-tight manner as soon as the male member 110 is removed therefrom. If the force applied to the operating portion 136 is released, the lock lever 130 elastically recovers. The male connector 100 and the female connector 200 each return to the initial state (see FIGS. 1A to 1D, 2A to 2D, 3A, and 3B).

In general, in a hospital where a plurality of patients are hospitalized, a pharmacist puts a drug solution prepared for each patient's site of administration into a syringe by suction. A nurse then administers the drug solution in the syringe to the patient through a catheter placed in the patient. In this case, if the syringe can be connected to any catheter, a misconnection accident may occur in which, for example, the nurse mistakenly connects the syringe storing a drug solution prepared for intravenous administration to a catheter placed in the bladder.

The connecting device 1 of the present embodiment can prevent such accidents. This will be described below.

As described above, the four ribs 127 are formed on the inner circumferential surface of the hood 120 of the male connector 100. The four grooves 257 are formed in the outer circumferential surface of the rotating cylinder 250 of the female connector 200. When the female connector 200 is inserted into the hood 120, the four ribs 127 fit into the four grooves 257 respectively. Thus, the male connector 100 can be connected to the female connector 200. If the rotating cylinder 250 does not have the grooves 257 corresponding to the ribs 127 of the hood 120, the female connector 200 cannot be inserted into the hood 120, and therefore, the male connector 100 cannot be connected to the female connector 200.

In the present embodiment, the four grooves 257 are formed in the rotating cylinder 250. In the present embodiment, for example, if at least one groove 257 of the four grooves 257 is omitted, the circumferential position of at least one groove 257 of the four grooves 257 is changed, the width of at least one groove 257 of the four grooves 257 is reduced, or the depth of at least one groove 257 of the four grooves 257 is reduced, then, the male connector 100 cannot be connected to the female connector 200.

Also, in the present embodiment, the four ribs 127 are formed in the hood 120. In the present embodiment, for example, if at least one rib 127 is added, the circumferential position of at least one rib 127 of the four ribs 127 is changed, the width of at least one rib 127 of the four ribs 127 is increased, or the protruding height of at least one rib 127 of the four ribs 127 is increased, then, the male connector 100 cannot be connected to the female connector 200.

Therefore, the number, circumferential position, dimensions (width and protruding height), and the like of ribs 127 formed in the hood 120 as well as the number, circumferential position, dimensions (width and depth), and the like of grooves 257 formed in the rotating cylinder 250 are standardized for each site (e.g., a vein, bladder, medullary cavity, gastrointestinal tract, or the like) to which the drug solution is to be administered. That is to say, connecting devices 1 that comply with a plurality of standards with different numbers, circumferential positions, dimensions, and the like of ribs 127 and grooves 257 are prepared for different sites to which the drug solution is to be administered. This allows a male connector to be selectively connected only to a female connector that complies with the same standard as the male connector. It is not possible to connect a male connector 100 that complies with a certain standard (e.g., a standard for intravenous administration) to a female connector 200 that complies with a different standard (e.g., a standard for bladder). As a result, the above-described misconnection accidents can be prevented.

It is relatively easy to produce a plurality of types of male connectors 100 that differ only in the number, circumferential position, dimensions, and the like of ribs 127 and to produce a plurality of types of female connectors 200 that differ only in the number, circumferential position, dimensions, and the like of grooves 257. Therefore, according to the present embodiment, misconnection accidents can be prevented with ease and at low cost.

It is sufficient that the rib(s) 127 and the groove(s) 257 are configured so as to allow a male connector and a female connector that comply with the same standard to be connected to each other but not allow a male connector and a female connector that comply with different standards to be connected to each other. The features of the rib(s) 127 and the groove(s) 257 that enable such selective connection are not limited to the number, circumferential position, and dimensions thereof. For example, the rib(s) 127 and the groove(s) 257 may have different cross-sectional shapes (shapes in cross sections along a horizontal plane) for different standards. Therefore, the features of the rib(s) 127 and the groove(s) 257 specified in each standard are not limited to the number, circumferential position, and dimensions, and any features can be specified. The number, circumferential positions, and dimensions of the ribs 127 and the grooves 257 shown in the present embodiment are merely examples, and any changes can be made thereto within the scope of the present invention. In general, it is preferable to realize selective connection between male connectors and female connectors by varying the number of ribs 127 and grooves 257. The reasons for this are that the worker can easily notice the difference in the number of ribs 127 and grooves 257, and it is relatively easy to produce male connectors 100 and female connectors 200 with different numbers of ribs 127 and grooves 257.

In the present embodiment, the ribs 127 extend from the distal end 121, or a position near the distal end 121, of the hood 120, and upper ends (starting ends) of the ribs 127 are located farther from the connecting cylinder 140 than the distal end 111 of the male member 110 in the vertical direction (or in other words, nearer to the distal end of the male connector 100 than the distal end 111) (see FIGS. 1A 1C). Moreover, the grooves 257 extend from the distal end (the position of the top plate 241), or a position near the distal end, of the female connector 200 (see FIG. 2A). Therefore, if an attempt is made to connect a male connector 100 to a female connector 200 that complies with a different standard than the standard with which this male connector 100 complies (that is, if a misconnection is attempted), the ribs 127 cannot be fitted into the grooves 257, and thus the female connector 200 cannot be substantially inserted into the hood 120. Unlike the present embodiment, if the ribs 127 extend from positions retracted from the distal end 121 of the hood 120 and/or the grooves 257 extend from positions away from the distal end of the female connector 200, it is possible to insert a portion of the female connector 200 into the hood 120 even when the ribs 127 cannot be fitted into the grooves 257. In this case, the convex portion 154 of the shield 150 may come into contact with the septum 220, causing the slit 153 of the shield 150 and/or the slit 223 of the septum 220 to open, and the drug solution may thus leak to the outside. In the case where the drug solution contains a hazardous drug, the worker will be exposed to the drug. The present embodiment can prevent these situations.

The ribs 127 extend in the direction of the central axis of the male connector 100, and the grooves 257 extend in the direction of the central axis of the female connector 200. Therefore, in the process of connecting the male connector 100 to the female connector 200 and in the process of disconnecting the male connector 100 from the female connector 200, while the ribs 127 are fitted in the grooves 257, the male connector 100 can move in the central axis direction (i.e., the longitudinal direction of the male member 110) relative to the female connector 200 (the female connector main body 210 and the rotating cylinder 250). Thus, the male connector 100 can be connected to and disconnected from the female connector 200 by simply moving (translating) the male connector 100 in the central axis direction relative to the female connector 200 (the female connector main body 210 and the rotating cylinder 250). This is advantageous in improving the ease of connecting and disconnecting operations.

The female connector 200 includes the rotating cylinder 250 that is rotatable around the female connector main body 210, and the grooves 257 and the opening 252 are formed in the rotating cylinder 250. Therefore, in a state in which the male connector 100 is connected to the female connector 200 (see FIGS. 4A and 4B), or in other words, in a state in which the ribs 127 are fitted in the grooves 257 and the claw 132 of the lock lever 130 is fitted in the opening 252, transmission of a rotational force between the male connector 100 and the female connector male connector 210 is blocked. For example, even if the catheter connected to the female connector main body 210 is twisted, the twisting does not loosen the screwing (see FIG. 4B) of the thread-lock connection between the connecting cylinder 140 and the barrel end 182. Moreover, even if the male connector 100 and the syringe 180 are rotated, the catheter connected to the female connector main body 210 does not twist, and loosening of the screwing of the thread-lock connection between the connecting cylinder 140 and the barrel end 182 caused by a torsional reaction force of the catheter does not occur.

The drug solution may possibly leak to the outside if the screwing of the thread-lock connection loosens. In the case where the drug solution contains a hazardous drug, the worker will be exposed to the drug. The present embodiment can prevent these situations.

The male connector 100 includes the lock lever 130 provided with the claw 132. The state in which the male connector 100 is connected to the female connector 200 is stably maintained by the engagement of the claw 132 with the female connector 200. The lock lever 130 with the claw 132 is advantageous in preventing the occurrence of unintentional disconnection of the male connector 100 from the female connector 200 and a resulting leakage of the drug solution from the male connector 100 and/or the female connector 200. In the case where the drug solution contains a hazardous drug, exposure of the worker to the drug can be prevented.

The claw 132 of the lock lever 130 engages with the rotating cylinder 250 rather than the female connector main body 210. Thus, as described above, in a state in which the claw 132 is engaged with the rotating cylinder 250, transmission of the rotational force between the male connector 100 and the female connector main body 210 is blocked.

The male connector 100 includes the shield 150 that closes the lateral holes 113 of the male member 110. Therefore, like a conventional male connector (see Patent Document 1), the male connector 100 can prevent leakage of the drug solution in the flow channel 112 to the outside when the female connector 200 is not connected thereto. The female connector 200 includes the septum 220 in which the slit 223 is formed. Therefore, like a conventional female connector (see Patent Document 1), the female connector 200 can prevent leakage of the drug solution in the flow channel 232 to the outside when the male connector 100 is not connected thereto. Accordingly, the connecting device 1 including the male connector 100 and the female connector 200 can be used as a closed-system connecting device. In a series of operations for transferring the drug solution in the syringe 180 to the catheter connected to the female connector 200, leakage of the drug solution to the outside is prevented. Even in the case where the drug solution contains a hazardous drug, the worker will not be exposed to the drug.

4. Various Modifications

The present invention is not limited to the above-described embodiment, and changes can be made thereto as appropriate.

In the above-described embodiment, in order to realize selective connection between male connectors and female connectors, the male connector 100 is provided with the ribs 127, and the female connector 200 is provided with the grooves 257. However, the present invention is not limited to this configuration. For example, a configuration may be adopted in which grooves are formed in the inner circumferential surface of the hood 120 of the male connector 100, and ribs that can fit into the grooves are formed on the outer circumferential surface of the rotating cylinder 250 of the female connector 200. In general, selective connection can be realized by providing the male connector and the female connector with respective fitting structures that can fit to each other when the male connector is connected to the female connector. It is preferable that, in a state in which a first fitting structure provided on the male connector and a second fitting structure provided on the female connector are fitted to each other, the first fitting structure can move in the central axis direction relative to the second fitting structure. It is preferable that the fitting of the first fitting structure to the second fitting structure is maintained as long as the female connector is inserted in the hood of the male connector. One of the first fitting structure and the second fitting structure may be a protrusion (e.g., a rib), and the other of the first fitting structure and the second fitting structure may be a depression (e.g., a groove) into which the protrusion can fit. Such protrusion and depression may have any length in the central axis direction, but it is preferable that at least one of the protrusion and the depression extends in the central axis direction.

In the above-described embodiment, the ribs 127 and the grooves 257 are varied according to the site to which the drug solution is to be administered; however, the present invention is not limited to this configuration. For example, the ribs 127 and the grooves 257 may be varied according to the type of the liquid flowing through the male connector and the female connector.

In the above-described embodiment, the claw 132 of the lock lever 130 engages with the rotating cylinder 250; however, the present invention is not limited to this configuration. The claw 132 may engage with the female connector main body 210 (the housing base 231). For example, it is possible to form a step (or a recess) on an exposed portion of the outer circumferential surface of the female connector main body 210 that is located nearer to the base end portion (nearer to the male luer 237) than the rotating cylinder 250 and cause the claw 132 to engage with this step (or recess). The claw 132 engaging with the female connector main body 210 is advantageous in counteracting a greater pulling force that is applied between the male connector 100 and the female connector 200 in a state in which the male connector 100 is connected to the female connector 200. The step (or recess) with which the claw 132 engages may be continuous over the entire circumference of the female connector main body 210 in the circumferential direction. In this case, while the claw 132 engages with the female connector main body 210, the male connector 100 can rotate relative to the female connector main body 210, and therefore, as in the case of the above-described embodiment, transmission of the rotational force between the male connector 100 and the female connector main body 210 is blocked.

Also, the configuration of the lock lever 130 provided in the male connector 100 is not limited to that shown in the above-described embodiment. Instead of the above-described lock lever 130, a known lock lever (see Patent Document 1, for example) to be provided in a male connector can be applied to the present invention. The number of lock levers is not limited to one, and may be two or more. When the claw 132 moves in the radial direction, the flange 115 that supports the lock lever 130 may elastically bend and deform, instead of the lock lever 130.

The shape of the opening at the distal end of the hood 120 is set to such a shape that enables the female connector 200 to be inserted into and removed from the hood 120 and enables the female connector 200 inserted in the hood 120 to be positioned in the horizontal direction. The shape of the opening at the distal end of the hood 120 is not limited to a circle such as that shown in the above-described embodiment. For example, the cross-sectional shape of the outer circumferential surface of the rotating cylinder 250 taken along a horizontal plane may be an ellipse, and, in this case, it is preferable that the shape of the opening at the distal end of the hood 120 is substantially the same ellipse as that of the rotating cylinder 250.

The cross-sectional shape of the inner circumferential surface of the hood 120 does not need to be constant in the central axis direction, and, for example, the inner diameter of the hood 120 may gradually increase toward the flange 115.

Also, the configuration of the shield 150 provided in the male connector 100 is not limited to that shown in the above-described embodiment. Instead of the self-closing slit 153, a hole (see Patent Document 1) through which the distal end 111 of the male member 110 is exposed may be formed at the distal end of the shield 150. In the present invention, the male connector 100 need not include the shield 150.

The male connector of the present invention may be connected to a member (e.g., a flexible tube and various containers) other than the syringe 180. Depending on the member to which the male connector is connected, the configuration of the base end portion (connecting cylinder 140) of the male connector can be changed as appropriate.

Also, the configuration of the female connector is not limited to that shown in the above-described embodiment. For example, the structure (the inner cylinder 233, the outer cylinder 234, and the locking cylinder 244) of a fixed portion of the cap 240 fixed to the housing base 231 can be changed as desired. The cylindrical surface 235 (see FIG. 2D) may be formed by the cap 240.

The configuration of the rotating cylinder 250 of the female connector can also be changed as desired. For example, instead of the opening 252, a recess that does not penetrate the rotating cylinder 250 in the radial direction may be formed in the outer circumferential surface of the rotating cylinder 250. The guide groove 253 may be omitted.

The female connector of the present invention may be connected to a member (e.g., a flexible tube) other than a catheter inserted in a patient. Depending on the member to which the female connector is connected, the configuration of the base end portion (the male luer 237, the outer cylinder 238, and the female thread 239) of the female connector can be changed as appropriate. In addition, the female connector of the present invention does not need to be connected to an end of a tube, and may be provided as a coinjection port in the middle of a tube, for example. Alternatively, the female connector of the present invention may be provided on an adapter (see Patent Document 2, for example) to be attached to a vial.

There is no limitation on the liquid flowing through the connecting device of the present invention. This liquid may be a drug solution containing no hazardous drug, blood, a nutrient, water (including physiological saline solution), various solutions, or the like.

INDUSTRIAL APPLICABILITY

The present invention can be widely used to form a flow channel through which a liquid flows. In particular, the present invention can be favorably used when it is necessary to prevent a misconnection between a male connector and a female connector. The present invention can be favorably used in the field of medicine. However, in addition to the field of medicine, the present invention can also be used in other fields in which liquids are handled, such as the fields of food, chemistry, machinery, and the like.

LIST OF REFERENCE NUMERALS

1 Connecting device
100 Male connector
110 Male member
111 Distal end of male member
113 Lateral hole (opening of flow channel)

112 Flow channel of male member
120 Hood
127 Rib (Projection, First fitting structure)
130 Lock lever
132 Claw
140 Connecting cylinder
142 Male thread
150 Shield
200 Female connector
210 Female connector main body
220 Septum (partition member)
223 Slit
250 Rotating cylinder
257 Groove (Second fitting structure)

The invention claimed is:

1. A connecting device comprising a male connector and a female connector that can be connected to and disconnected from each other,
wherein the male connector includes:
a rod-shaped male member;
a hood surrounding the male member; and
a first fitting structure provided on an inner circumferential surface of the hood,
the female connector includes:
a female connector main body including a partition member in which a slit is formed, the partition member being made of an elastic material;
a rotating cylinder provided on the female connector main body so as to be rotatable around the female connector main body; and
a second fitting structure provided on an outer circumferential surface of the rotating cylinder, and
when the male connector is connected to the female connector, the male member passes through the slit of the partition member, the female connector is inserted into the hood, and the first fitting structure fits to the second fitting structure.

2. The connecting device according to claim 1, wherein the female connector cannot be inserted into the hood when the first fitting structure does not fit to the second fitting structure.

3. The connecting device according to claim 1, wherein the first fitting structure is provided nearer to a distal end of the male connector than a distal end of the male member.

4. The connecting device according to claim 1, wherein the second fitting structure is provided at or near a distal end of the female connector.

5. The connecting device according to claim 1, wherein, in a process of connecting the male connector to the female connector and in a process of disconnecting the male connector from the female connector, the male connector is movable in a longitudinal direction of the male member relative to the female connector, with the first fitting structure being fitted to the second fitting structure.

6. The connecting device according to claim 1, wherein one of the first fitting structure and the second fitting structure is a groove extending in a direction in which the male connector is connected to and disconnected from the female connector, and
another one of the first fitting structure and the second fitting structure is a projection that can fit into the groove.

7. The connecting device according to claim 1, wherein, in a state in which the male connector is connected to the female connector, the male connector is rotatable relative to the female connector main body.

8. The connecting device according to claim 1, wherein the male connector further includes a lock lever and a claw provided on the lock lever,
the claw is elastically displaceable in a direction away from the male member, and
when the male connector is connected to the female connector, the claw engages with the female connector.

9. The connecting device according to claim 8, wherein, when the male connector is connected to the female connector, the claw engages with the rotating cylinder.

10. The connecting device according to claim 1, wherein the male connector further includes a shield that is compressively deformable in a longitudinal direction of the male member,
in a state in which the male connector is not connected to the female connector, the shield closes an opening of a flow channel provided in the male member, and
in a state in which the male connector is connected to the female connector, the shield is compressively deformed in the longitudinal direction of the male member, and the male member protrudes from the shield.

11. The connecting device according to claim 1, wherein the male connector further includes, on a side opposite to the male member, a connecting cylinder that is disposed coaxially with the male member and is in communication with the male member, and
a male thread is formed on an outer circumferential surface of the connecting cylinder.

* * * * *